United States Patent [19]

Wu

[11] Patent Number: 5,869,089
[45] Date of Patent: Feb. 9, 1999

[54] MANUFACTURING METHOD OF PROGRAMMABLE TRANSDERMAL THERAPEUTIC SYSTEM

[75] Inventor: Risheng Wu, Beijing, China

[73] Assignee: China-America Technology Corp. (CTC), New York, N.Y.

[21] Appl. No.: 949,221

[22] Filed: Oct. 10, 1997

Related U.S. Application Data

[63] Continuation of Ser. No. 621,730, Mar. 21, 1996, abandoned.

[51] Int. Cl.$^6$ .................................................. A61L 9/70
[52] U.S. Cl. ........................................ 424/449; 424/448
[58] Field of Search .................................... 424/448, 449

[56] References Cited

U.S. PATENT DOCUMENTS

| | | | |
|---|---|---|---|
| 4,201,211 | 5/1980 | Chandrasekaran et al. | 128/268 |
| 4,904,475 | 2/1990 | Gale et al. | 424/449 |
| 5,230,898 | 7/1993 | Horstmann | 424/449 |
| 5,310,559 | 5/1994 | Shah et al. | 424/448 |

*Primary Examiner*—Thurman K. Page
*Assistant Examiner*—Kathryne E. Shelborne
*Attorney, Agent, or Firm*—Dilworth & Barrese

[57] ABSTRACT

A novel manufacturing method for membrane controlled programmable trans-dermal therapeutic systems (PTTS) comprises highly stabilized supersaturated drug solid solution system and easily adjustable controlled release membrane. The features of the programmable transdermal therapeutic system are as follows:

1. The PTTS release drugs continuously through the skin with long duration into the systemic blood circulating system with adequate therapeutic effect.
2. The release rate of the TTS can be pre-programmed to decrease day by day according to a schedule of decreased symptoms, so side effects may be relieved greatly.

15 Claims, No Drawings

MANUFACTURING METHOD OF PROGRAMMABLE TRANSDERMAL THERAPEUTIC SYSTEM

This is a continuation of application Ser. No. 08/621,730 filed on Mar. 21, 1996, now abandoned.

BACKGROUND OF THE INVENTION

This invention relates to programmable transdermal therapeutic systems (PTTS) and to manufacturing programmable transdermal therapeutic systems (PTTS) or transdermal patches, which comprise drug reservoirs of highly stabilized supersaturated drug solid polymer solution and a controlled release membrane with an easily adjustable release rate.

After the marketing of transdermal therapeutic systems (TTS) since the 1980's, TTS have been developed rapidly, owing to certain advantages not provided by traditional methods of drug administration.

TTS can steadily control (one day to one week) an adequate constant release dose rate of drug into the systemic blood circulating system, without the presence of peaks and valleys in blood drug concentration, irritation of gastric and intestinal tracts, and the first-pass effect of liver.

TTS also can be used conveniently with high patient compliance. This is so since TTS having advanced technology of release rate by controlled membrane can administer drug with a pre-determined adequate release rate and with minimal influence based on the varying permeability of skin which occurs at different sites and in different patients. The following commercially available TTS belong to the type of membrane controlled TTS: Transderm-Nitro™ (nitroglycerin TTS); Transderm-Scop™ (scoplamine TTS); Estraderm™ (estradiol TTS); Catapres-TTS™ (clonidine TTS); Nicoderm™ (nicotine TTS).

The long acting (several days to one week) membrane controlled TTS with effective and steady drug administration (such as clonidine TTS) incorporate a clonidine saturated solid polymer solution in the presence of excess fine clonidine particles as drug reservoir (U.S. Pat. No. 4,201,211), to insure extended duration of drug saturated state that maintains a constant drug concentration and concentration gradient for a required constant zero order release rate of drug.

However, some symptoms require not only long acting duration of drug administration, but also a decreasing dosage rate which automatically corresponds to a schedule of decreased symptoms, i.e., an adequate pre-determined program of release dose rate of drug, to greatly relieve side effects. An example is clonidine (a non-opiate detoxification drug) therapy in opiate withdrawal syndrome.

SUMMARY OF THE INVENTION

The present invention provides a transdermal drug delivery device comprising at least one drug reservoir which includes a supersaturated combination of drug and solid polymer, and at least one control release membrane for controlling release of drug which is in contact with the at least one drug reservoir.

In another aspect a method of manufacturing a transdermal delivery device is provided which includes providing a coating composition which includes a supersaturated combination of drug and solid polymer;

coating the coating composition on a film backing and forming a layer of coating composition;

applying a control release membrane to the layer of coating composition;

applying a contact adhesive layer to the control release membrane; and applying a release liner to the contact adhesive layer.

In yet another aspect of the present invention a method of reducing opiate withdrawal symptoms is provided which includes administering a transdermal drug delivery device as. described above which contains clonidine to a patient addicted to an opiate.

DETAILED DESCRIPTION OF THE INVENTION

For maintaining a higher initial release dose rate of TTS and then decreasing the release dose rate according to a pre-programmed schedule, a prerequisite maintenance of high drug concentration. For the relatively lower solubility of drug in high polymers, it is necessary to form the required high concentration in the supersaturated state. Long term stability is not feasible in the liquid state, but is achieved in the highly stabilized supersaturated state. This supersaturated state can only be realized in solid polymer solution with specialized technology and conditions.

This invention adopts a series of special technology which provides formation of a highly stabilized supersaturated solid polymer solution. This is the basic prerequisite for realizing a TTS with high initial release rate and decreasing release rate with time. In order to realize the requirement of decreasing release rate with a pre-determined schedule, it is necessary to use a type of controlled release membrane with correspondingly matched release rate selected from a series of controlled release membranes with easily adjustable release rate in broad range. This type of controlled release membrane can be selected from the series of novel nuclear track microporous membrane made from alpha particles, rather from the traditional nuclear fission fragments of nuclear reactor (Risheng Wu & Jianhuan Zhu: A Nuclear Track Microporous Membrane. Nucl. Tracks Radiat. Meas. vol. 22, pp. 933–935, 1993; Chinese Patent: CN-1079414) incorporated herein by reference, or from the series of the modified EVA membrane (pending Chinese patent). Then the programmable TTS can be prepared according to the method described in the literature (Risheng Wu et al. Application of new nuclear track microporous membrane in transdermal therapeutic system Nucl. Tracks Radiat. Meas. vol. 22, pp 937–939, 1993; Chinese Patent: CN-1080524) both incorporated herein by reference.

The rate or slope of decreasing release rates can be controlled with the selection of critical controlled release membrane from the series of controlled membranes with different release rates.

The following examples are set forth herein for illustrative purposes only and are not to be construed as limiting either the spirit or scope of the invention as later recited in the claims.

EXAMPLE

Manufacturing Technology of Programmable TTS for the total manufacture of 1000 pieces of TTS:

FORMULATION

| Material | Drug Reservoir Coating Composition | Contact Adhesive Layer Coating Composition |
|---|---|---|
| Clonidine | 1.4 g | 0.20 g |
| Polyacrylate Pressure Sensitive Adhesive (Model PSA-803*) | 33.33 g | 33.33 g |
| Ethyl Acetate | 60 g | 100 g |

*Manufactured by Beijing Clepsydrae Therapeutic System Co., Ltd.

Polyacylate pressure sensitive adhesive includes butyl acrylate monomer, ethylhexyl acrylate monomer, vinyl acetate monomer, 2-methyl acrylic acid monomer, and acryl amide monomer. A preferred formulation provides butyl acrylate about 16 kg ethylhexyl acrylate about 19 kg, vinyl acetate about 11 kg, 2-methyl acrylic acid about 0.45 kg and acryl amide about 0.38 kg. The above monomers are polymerized in a solvent such as ethyl acetate about 108 kg in the presence of an initiator such as about 0.086 kg Azobisisobutylnitrile.

Controlled Release Membrane: Nuclear Track Microporous Membrane Model NTMM-53, Beijing Clepsydrae Therapeutic System Co. Ltd. or Modified EVA Membrane Model MEVA-48, Beijing Clepsydrae Therapeutic System Co. Ltd. NTMM-53 has a porosity of about $4.5 \times 10^5$ holes/cm$^2$ with a hole diameter of about 2 $\mu$m and a film thickness of about 10 $\mu$m polycarbonate. Processing Technology:

According to the formulation of the above Drug Reservoir Coating Composition and Contact Adhesive Coating Composition, 1.4 g and 0.20 g of clonidine were dissolved in 60 g and 100 g of ethyl acetate correspondingly. Each of the two solutions were mixed homogeneously with 33.33 g (dry basis of Polyacrylate Sensitive Adhesive, separately). The two coating compositions were sealed in containers and were ready for coating.

The above two coating compositions were coated separately to form a homogeneous 50 $\mu$m dry film layer on polyester film backing and silicone based release liner respectively. Then the two coated sheets are dried in a drying channel with a temperature increasing gradient of about 10° C. every 10 min., the maximum temperature is about 80° C., and the total drying time is about 1 hour. The clonidine must not be crystallized out to form nontransparent layer. In the normal situation, the two dried films are formed as supersaturated solid polymer drug solution. If non-transparent films are formed, it indicates that conversion into a saturated state has occurred, and such non-transparent films should not be used as programmable TTS herein.

The above two coated film layers are laminated with the mentioned controlled release membrane according to the arranged order of polyester film backing/drug reservoir/controlled release membrane/contact adhesive layer/release liner, to form laminated sheets that are cut with a die, to form the programmable TTS with a preferred patch area of about 2.3 cm$^2$.

The release rates of the above programmable clonidine TTS decrease according to the following programmed order

| First day: | 0.17 mg/day, |
| Second day: | 0.13 mg/day; |
| Third day: | 0.09 mg/day; |
| Fourth day: | 0.06 mg/day; |
| Fifth day: | 0.04 mg/day; |
| Sixth day: | 0.02 mg/day; |

The rate or slope of decreasing release rates day by day can be adjusted with the use of other commercially available models of nuclear track microporous membrane (NTMM) or other models of modified EVA membrane (MEVA) with different release rates.

What is claimed is:

1. A transdermal drug delivery device comprising at least one drug reservoir which includes a supersaturated combination of drug and solid polymer, and at least one control release membrane for controlling release of drug which is in contact with the at least one drug reservoir, wherein the control release membrane is a nuclear track microporous membrane made from alpha particles or a modified EVA membrane.

2. A transdermal drug delivery device according to claim 1 further comprising a series of control release membranes wherein each membrane contained therein has a different release rate.

3. A transdermal drug delivery device according to claim 1 wherein the device releases drug at a decreasing release rate over time.

4. A transdermal drug delivery device according to claim 1 comprising a film backing, one drug reservoir, the control release membrane, a contact adhesive layer, and a release liner.

5. A transdermal drug delivery device according to claim 1 wherein the drug is clonidine.

6. A transdermal drug delivery device according to claim 1 wherein the polymer is a copolymer manufactured from butyl acrylate, ethylhexyl acrylate, vinyl acetate, 2-methyl acrylic acid and acryl amide.

7. A transdermal drug delivery device according to claim 1 wherein the control release membrane has a porosity of about $4.5 \times 10^5$ holes/cm$^2$ with a hole diameter of about 2.0 $\mu$m and a thickness of about 10 $\mu$m.

8. A method of manufacturing a transdermal drug delivery device comprising:

providing a coating composition which includes a supersaturated combination of drug and solid polymer;

coating the coating composition on a film backing and forming a layer of coating composition;

drying the coating composition on said film backing with a temperature increasing gradient of about 10° C. every 10 minutes, wherein the maximum final temperature is about 80° C. and the total drying time is about 1 hour;

applying a control release membrane to the layer of coating composition;

applying a contact adhesive layer to the control release membrane; and applying a release liner to the contact adhesive layer.

9. A transdermal drug delivery device according to claim 8 wherein the coating composition is manufactured by mixing the drug in a solvent to form a mixture and combining the mixture with the solid polymer to form a supersaturated drug/polymer mixture.

10. A transdermal drug delivery device according to claim 8 wherein the solid polymer is a copolymer manufactured from butyl acrylate, ethylhexyl acrylate, vinyl acetate, 2-methyl acrylic acid and acryl amide.

11. A method according to claim 9 wherein the solvent is ethyl acetate.

12. A method accordingly to claim 8 wherein the drug is clonidine.

13. A method accordingly to claim 8 wherein the contact adhesive layer is manufactured by combining the drug with a solid polymer by mixing the drug in a solvent to form a mixture and combining the mixture with the solid polymer to form a supersaturated polymer/drug mixture.

14. A method of reducing opiate withdrawal symptoms comprising administering a transdermal drug delivery device according to claim 5 to a patient addicted to an opiate.

15. A method of reducing opiate withdrawal according to claim 14 wherein release of clonidine from the device gradually decreases over time.

* * * * *